United States Patent [19]

Totten et al.

[11] 4,316,041
[45] Feb. 16, 1982

[54] LIQUID CRYSTAL SILANES

[75] Inventors: George E. Totten, West Haverstraw, N.Y.; Thomas C. Williams, Ridgefield, Conn.

[73] Assignee: Union Carbide Corporation, New York, N.Y.

[21] Appl. No.: 122,482

[22] Filed: Feb. 19, 1980

[51] Int. Cl.$^3$ .................. C09K 3/34; G02F 1/13; C07F 7/10

[52] U.S. Cl. .................. 556/420; 252/299.4; 252/299.62; 252/299.64; 252/299.67; 252/299.68; 252/299.7; 260/192; 260/194; 260/195; 260/196; 260/197; 260/199; 260/202; 260/207; 260/207.1; 260/205; 260/397.2; 350/340; 350/341; 350/350 R; 428/1; 556/421

[58] Field of Search .............. 252/299.4, 408, 299.64, 252/299.67, 299.68, 299.7, 299.62, 299.63; 350/340, 341, 350 R, 350 S; 556/419, 420, 421; 428/1

[56] References Cited

U.S. PATENT DOCUMENTS

| | | | |
|---|---|---|---|
| 2,907,782 | 10/1959 | Pike | 556/421 |
| 3,494,951 | 2/1970 | Berger | 556/420 |
| 3,728,008 | 4/1973 | Allan et al. | 350/340 |
| 3,854,793 | 12/1974 | Kahn | 350/340 |
| 3,904,373 | 9/1975 | Harper | 252/408 |
| 3,950,588 | 4/1976 | McDougal | 556/420 |
| 3,973,057 | 8/1976 | Channin et al. | 350/340 |
| 3,979,319 | 9/1976 | Fukai et al. | 252/299.4 |
| 3,991,241 | 11/1976 | Matsumoto et al. | 350/340 |
| 4,046,794 | 9/1977 | Pepe et al. | 556/421 |
| 4,088,670 | 5/1978 | Bargain et al. | 556/421 |
| 4,151,326 | 4/1979 | Fumada et al. | 252/299.4 |
| 4,203,952 | 5/1980 | Hancock et al. | 252/408 |

FOREIGN PATENT DOCUMENTS

| | | | |
|---|---|---|---|
| 2635630 | 2/1977 | Fed. Rep. of Germany | 350/341 |
| 48-94693 | 12/1973 | Japan | 252/299.4 |
| 52-76050 | 6/2977 | Japan | 252/299.4 |
| 1532295 | 11/1978 | United Kingdom | 252/408 |

OTHER PUBLICATIONS

Young, W. R. et al., Mol. Cryst. Liq. Cryst. vol. 13, pp. 305–321 (1971).
Harper, G. B., Anal. Chem., vol. 47, No. 2, pp. 348–351 (Feb. 1975).
Kahn, F. J., et al.; Proc. IEEE., vol. 61, No. 7, pp. 823–828 (Jul. 1973).
Usol Tseva, V. A. et al., Russ. Chem. Rev., vol. 32, No. 9, pp. 495–507 (Sep. 1963).
Demus, D., Nonemissive Electrooptic Displays, pp. 83–119 (1975).

*Primary Examiner*—Teddy S. Gron
*Attorney, Agent, or Firm*—Eugene G. Trautlein

[57] ABSTRACT

Silicon based liquid crystal compounds produced by the reaction of an isocyanatosilane with a Schiff base, aromatic ester, azo compound or cholesteryl compound. The liquid crystals are useful in those applications in which liquid crystals are currently used and they also have the capability of being firmly chemically bonded to certain substrates, such as glass, thus avoiding the need for hermetic sealing.

14 Claims, No Drawings

LIQUID CRYSTAL SILANES

BACKGROUND OF THE INVENTION

The majority of pure crystalline organic compounds generally melt from the solid form to an isotropic liquid with temperature changes of less than 1° C. This drastic change from ordered crystal to disordered liquid occurs so suddenly because the intermolecular forces in the crystal are about the same in all dimensions and therefore are overcome by the increasing thermal energy of the system at about the same time.

In some organic crystals, the transition from crystal state to true, i.e. isotropic, liquid state is separated by intermediate states which may be stable over various temperature intervals. In these intermediate states, which are termed mesomorphic, the molecules retain crystalline order along one or two dimensions and show liquid disorder in the remaining directions. In the mesomorphic states, the compound displays highly anisotropic properties and is said to be a liquid crystal.

Liquid crystal compounds have become the basis of a large and growing technological field. Their value arises from their unique physical properties. In the liquid crystal or mesomorphic state the molecules assume preferred relative orientations. These orientations are precise and reproducible under controlled conditions. By various means, the liquid crystal molecules can be shifted from one spacial orientation to another or from ordered states to disordered states and back again. Shifts can be accomplished within milliseconds and even microseconds and can be induced by changes in temperature, pressure, electric and magnetic fields and other conditions. When liquid crystal molecules are shifted from one orientation to another, the electromagnetic properties in a given direction are changed and impinging radiation can thereby be transmitted, blocked, absorbed, emitted, reflected or selectivity filtered.

Because of these highly useful properties liquid crystals have found use in many applications such as optical filters, electroptical displays and thermal sensing devices.

One problem which has plagued the liquid crystal art has been the need to hermetically seal liquid crystals in a cell cavity before use.

Because of the many uses of liquid crystals, new compounds which display liquid crystalline behavior are being continuously sought. Furthermore, any liquid crystal which can be chemically bonded to a substrate and therefore eliminate the need for hermetic sealing would be highly desirable.

SUMMARY OF THE INVENTION

It has now been found that certain hereinafter more fully defined alkoxy-, chloro-, or dimethylaminosilyl-substituted compounds exhibit liquid crystalline behavior. It has been also found that these novel liquid crystals can be directly chemically bonded to certain substrates.

DESCRIPTION OF THE INVENTION

The liquid crystal compositions of this invention are the compounds of the general formula:

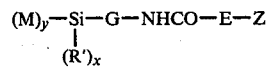

wherein y is an integer having a value of from 1 to 3; x is an integer having a value of from 0 to 2; M is methoxy, ethoxy, chloro or dimethylamino; R' is hydrogen, methyl, or ethyl; G is alkylene having from 2 to 4 carbon atoms or arylene or aralkylene having from 6 to 8 carbon atoms; E is —O— or —NH—; and Z is a group of the formula:

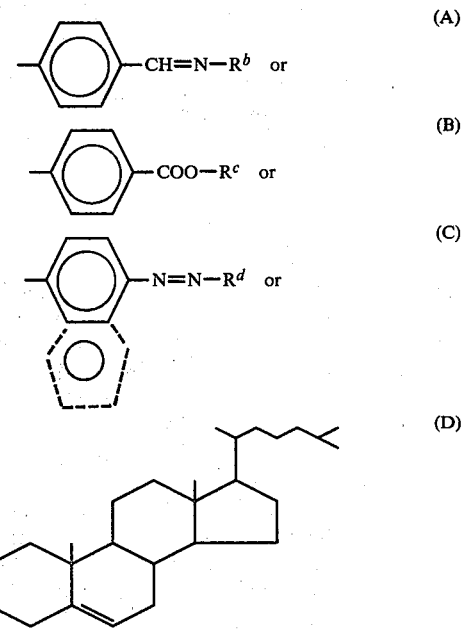

wherein $R^b$ is an unsubstituted or substituted phenyl, fluorenyl, fluorenonyl or anthracenyl group; $R^c$ is an unsubstituted or substituted phenyl group; and $R^d$ is an unsubstituted or substituted phenyl, naphthyl or anthracenyl group; wherein the substituents on said groups can be any organic or inorganic group which does not interfere with the liquid crystal or mesomorphic state of the silyl compound (I), such as chloro, nitro, methylthio, bromo, iodo, tertiary amino, acyl having from 2 to 12 carbon atoms, dialkylamino in which the alkyl group has from 1 to 5 carbon atoms, alkoxy having from 1 to 6 carbon atoms, alkyl having from 1 to 10 carbon atoms, preferably 1 to 4 carbon atoms, cyano, esters which may contain substituted aryl or aralkyl moieties of from 1 to 12 carbon atoms, or carbonates containing an alkyl group of from 1 to 10 carbon atoms.

As can be seen from the above, the liquid crystals of this invention can be represented by four groups termed (A) the Schiff-base-type, (B) the ester type, (C) the azo-type and (D) the cholesteryl type.

Schiff-base-type liquid crystals

The Schiff-base-type liquid crystal compounds of this invention can be represented by the subgeneric formula:

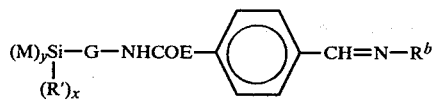 (II)

The compounds are produced by the reaction of a silane of the formula:

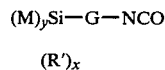 (II A)

with an hydroxyl or amino compound of the formulas

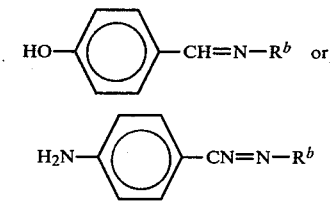 (II B)

or

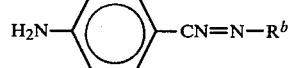 (II C)

Illustrative of suitable isocyanato silanes of Formula (II A) one can mention gamma-isocyanatopropyltrimethoxysilane, gamma-isocyanatopropylmethyldimethoxysilane, gamma-isocyanatopropyltriethoxysilane, gamma-isocyanatopropyldimethylmethoxysilane, gamma-isocyanatopropylmethyldiethoxysilane, gamma-isocyanatopropyldimethylethoxysilane, beta-isocyanatoethyltrimethoxysilane, delta-isocyanatobutylmethyldimethoxysilane, 3-isocyanatophenyldimethylmethoxysilane, 2-(3-isocyanatophenyl)ethyltriethoxysilane, gamma-isocyanatopropyldimethylaminosilane, gamma-isocyanatopropylchlorosilane, gamma-isocyanatopropyldimethoxysilane, gamma-isocyanatopropylmethyldichlorosilane, beta-isocyanatopropyldiethyldimethylaminosilane, beta-isocyanatoethyldiethoxysilane, beta-isocyanatoethyldimethylchlorosilane, beta-isocyanatoethylmethyldichlorosilane, delta-isocyanatobutyltriethoxysilane, delta-isocyanatobutylmethyldichlorosilane, delta-isocyanatobutyldiethyldimethylaminosilane, 2-(3-isocyanatophenyl)ethyldichlorosilane, 2-(3-isocyanatophenyl)ethyldimethylaminosilane, and the like.

Illustrative of the Schiff-base type liquid crystals of this invention one can name:

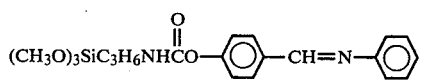

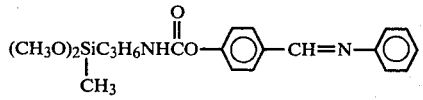

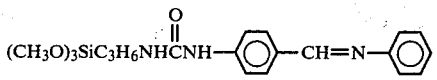

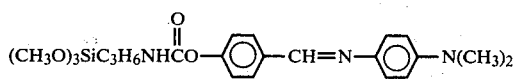

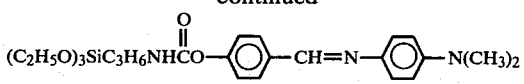

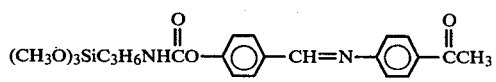

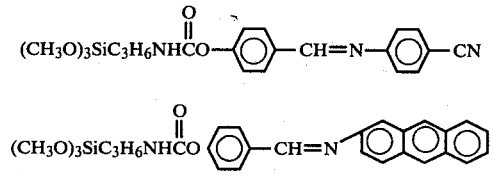

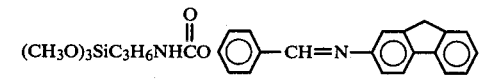

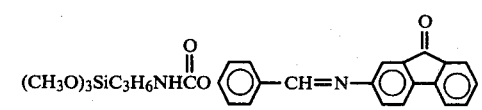

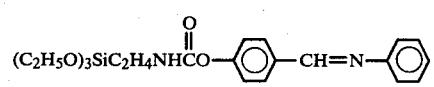

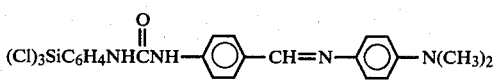

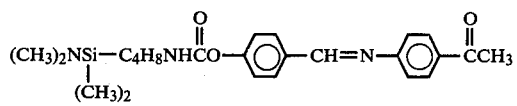

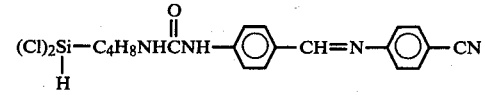

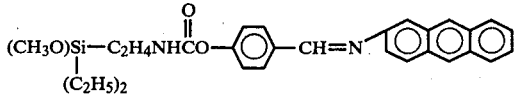

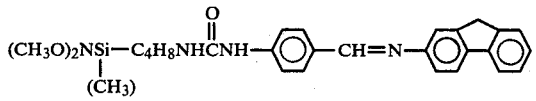

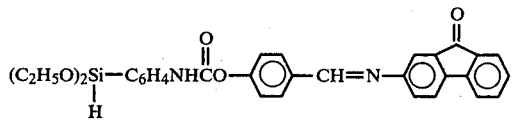

Among the many compounds suitable for the production of Schiff-base type liquid crystals of this invention one can name p-dimethylamino-benzylidine-p-hydroxyaniline, p-methoxy-benzilidene-p-hydroxyaniline, p-cyanobenzilidene-p-hydroxy-aniline, p-hydroxy-benzilidene-4-amino-a-fluorenone, p-hydroxy-benzilidene-1-aminoanthracene, and the like.

Ester-type liquid crystals

The ester-type liquid crystal compounds of this invention can be represented by the subgeneric formula:

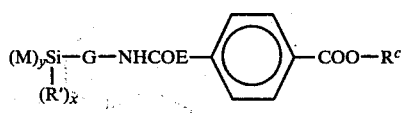            (III)

They are produced by the reaction of the silanes shown useful for producing compounds (II) and an hydroxyl or amino compound of the formulas:

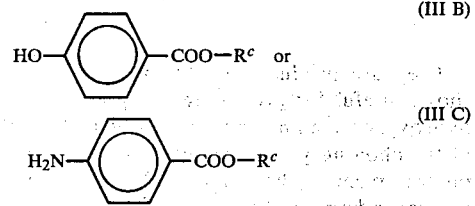

Illustrative of the ester type liquid crystals of this invention one can name:

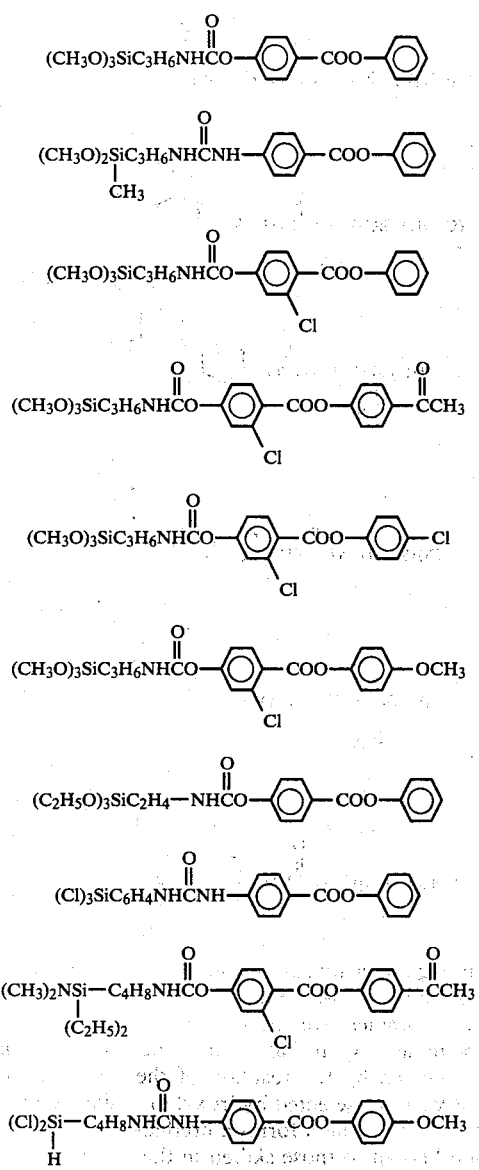

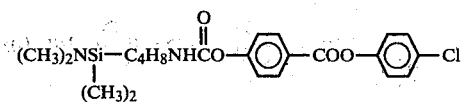

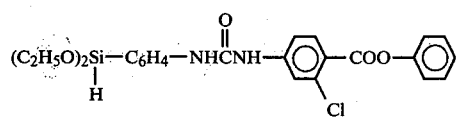

Among the many compounds suitable for the production of ester-type liquid crystals of this invention one can name 2-chloro-4-hydroxy-(p-acetylphenyl) benzoate, 2-chloro-4-hydroxy-cyano benzoate, 2-chloro-4-hydroxy-p-chlorobenzoate, 2-chloro-4-hydroxy-(p-methoxy)benzoate, 4-aminophenyl-benzoate, 4-hydroxyphenylbenzoate and the like.

Azo-type liquid crystals

The azo-type liquid crystal compounds of this invention can be represented by the subgeneric formula:

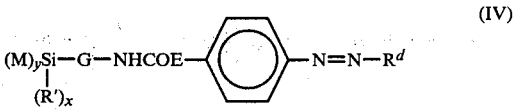            (IV)

These are produced by the reaction of the silanes shown useful for producing compounds (II) and an hydroxyl or amino compound of the formulas:

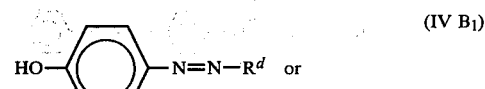            (IV B$_1$)

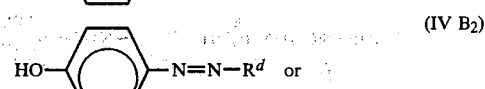            (IV B$_2$)

            (IV C$_1$)

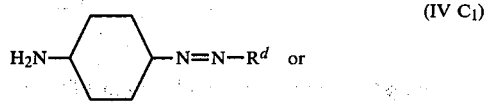            (IV C$_2$)

Illustrative of the azo-type liquid crystals of this invention one can name:

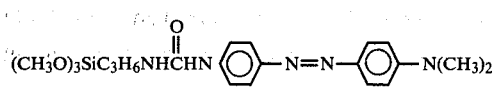

-continued

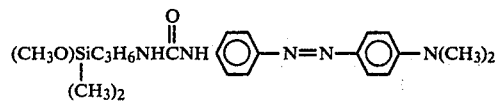

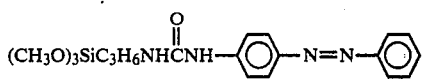

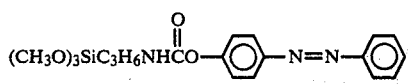

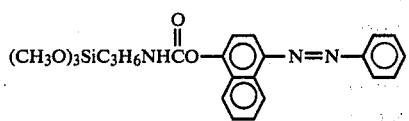

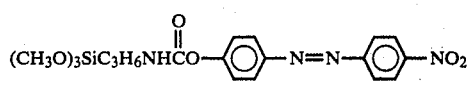

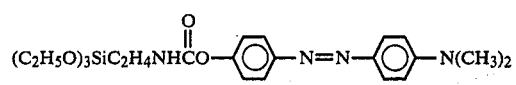

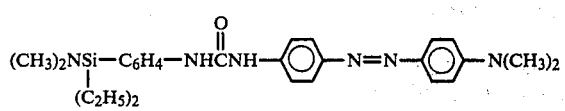

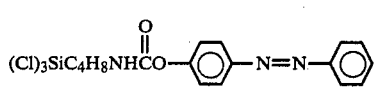

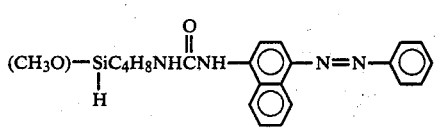

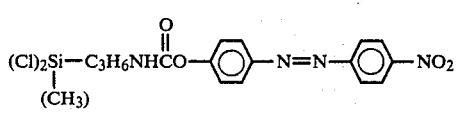

Among the many compounds suitable for the production of azo-type liquid crystals of this invention one can name N,N-dimethylamino-4,4′-azodianiline, p-phenylazophenol, p-phenylazoaniline, p-nitrophenylazoaniline, and the like.

In the formulas for compounds (II) to (IV), the phenyl and naphthyl groups can be unsubstituted or substituted, as previously disclosed.

Cholesteryl-type liquid crystals

The cholesteryl type liquid crystal compounds of this invention can be represented by the subgeneric formula:

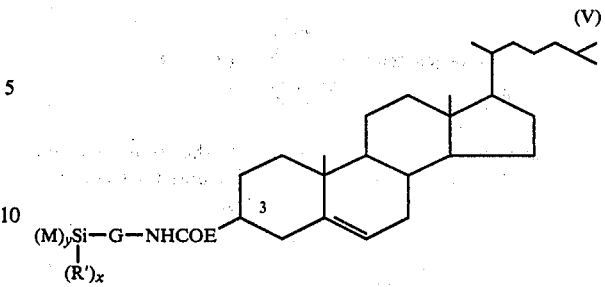

They are produced by the reaction of the silanes shown useful for producing compounds (II) and a 3-hydroxyl or 3-amino cholesterol compound. Illustrative of the cholesteryl type liquid crystals of this invention one can mention those indicated below as well as their corresponding substituted derivatives containing substituents on the cholesteryl nucleus:

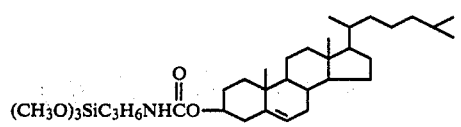

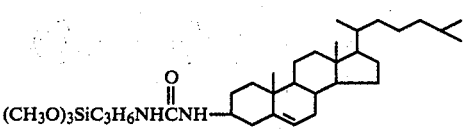

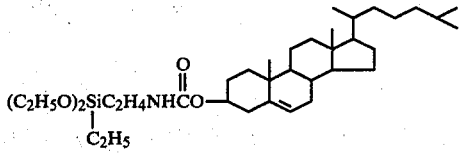

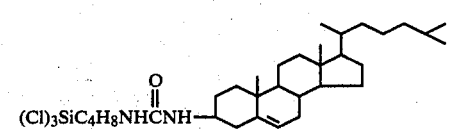

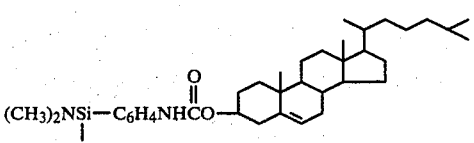

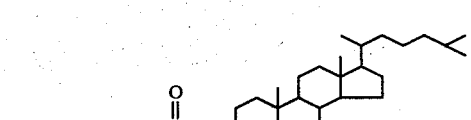

Among the many compounds suitable for the production of cholesteryl-type liquid crystals of this invention one name cholesterol, cholestanol, and the like.

The liquid crystal silane compounds of this invention are produced by the reaction of the isocyanate compound with the selected hydroxyl or amino compound. This reaction, which forms a urethane or urea linkage, is well known to those skilled in the art as well as the conditions under which it is carried out, including the catalysts often used in such reaction.

The reaction of the isocyanate-substituted silane and the compound having one of the above-described functional hydroxyl or amino group is preferably carried out in an inert solvent. Among the many suitable solvents one can name tetrahydrofuran, triethylamine, dioxane, 2-butanone, toluene, acetonitrile, di-isopropyl ether and dimethoxy ethane. Of course, mixtures of solvents can also be used and, as is known, under essentially anhydrous conditions due to the presence of the isocyanato group.

The reaction can be carried out at subatmospheric, atmospheric, or superatmospheric pressure. The temperature of the reaction can be from 20° C. to 80° C., preferably from 40° C. to 60° C. The reaction can be carried out in an inert atmosphere such as nitrogen or argon. The time of the reaction will vary and will depend upon the size of the batch, the reaction parameters chosen and the specific compounds employed in the reaction.

The mole ratio of isocyanate-substituted silane of the compound having the hydroxyl or amino functional group can be from 3:1 to 1:1, preferably from 1.1:1 to 1:1.

In a typical procedure for producing the liquid crystal silanes of this invention the isocyanato-substituted silane and the compound containing the functional hydroxyl or amino group are charged to a flask under nitrogen, along with a solvent. This reaction mixture is heated then cooled to room temperature and the solvent removed under vacuum. The liquid crystal silane is then recovered by conventional means.

The liquid crystals of this invention can also be in polymeric form. Polymerization is accomplished by the introduction into the reaction mixture of a suitable polymerizing catalyst. These catalysts and their useful amounts are well known to those skilled in the art but nevertheless one can name azobisisobutyronitrile, dicumyl peroxide, cumene hydroperoxide, t-butylhydroperoxide, benzoyl peroxide, bis(p-chlorobenzyl)-peroxide and the like.

It was found that the liquid crystal silanes of this invention can be chemically bonded to or coated on suitable substrates such as glass, silica and silicious substrates or on these substrates which had been surface coated with oxides of tin, indium or mixtures thereof. The bonding is accomplished by mixing the liquid crystal silanes of this invention with an inert solvent and glacial acetic acid, slowly adding distilled water in a large excess, preferably a molar ratio of $\geq 100$ to 1, followed by coating of the substrate with this mixture and drying of the coated substrate at from 20° C. to 110° C., preferably from 75° to 90° C. for from 2 hours to 48 hours, preferably from 16 hours to 24 hours. A film, which exhibits liquid crystalline behavior, and which is chemically bonded to the substrate is formed on the surface of the substrate.

The novel liquid crystals of this invention are useful in the many applications in which liquid crystals are employed. Further, the liquid crystals of this invention can be directly chemically bonded to a substrate thereby overcoming a longstanding problem in the art. It was completely unexpected and unobvious to find that the compounds disclosed herein would exhibit liquid crystalline behavior and it was also completely unexpected and unobvious to find that these compounds could be chemically bonded to a substrate without the loss of liquid crystal capability.

The following examples serve to further illustrate the invention. In the examples, the concentrations are in parts by weight unless otherwise specified. In the examples the mesophase was detected using variable temperature polarized light photomicroscopy, a procedure well known to those in this field. This procedure involves heating the liquid crystal silane compound on a hot stage from ambient temperature through its mesophases until an isotropic condition is observed. Thus a solid sample is heated until a birefringent liquid appears; this temperature is designated $T_1$. The sample is further heated until a non-birefringent isotropic condition exists, at a temperature designated $T_2$. The mesophase or liquid crystalline behavior thus occurs between $T_1$ and $T_2$ and the mesophase temperature range is the range from $T_1$ to $T_2$. The existence of a mesophase observed by variable temperature photomicroscopy was verified by the presence of corresponding endotherms for $T_1$ and $T_2$ by differential scanning calorimetric analysis.

EXAMPLE 1

There were charged to a 250 ml, three-neck round bottom flask equipped with a magnetic stirrer, thermometer and water condenser and in which there was an inert argon atmosphere, 9 parts by weight of γ-isocyanatopropyltrimethoxysilane, 10 parts by weight of p-dimethylaminobenzylidine-p-hydroxyaniline, 40 parts by weight of tetrahydrofuran and 0.5 part by weight of triethylamine. The reaction mixture was refluxed for 5 hours under argon and then cooled. The tetrahydrofuran and triethylamine were removed from the reaction mixture under vacuum at 50° C. and less than 1 mm Hg pressure. The chemical structure of the resulting liquid crystal product, characterized by infrared spectroscopy and carbon-13-nuclear magnetic resonance spectroscopy was:

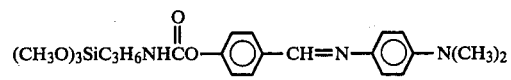

The liquid crystal had a mesophase of from 40° C. to 112° C.; by variable temperature photomicroscopy and confirmed by differential scanning calorimetry analysis.

In a similar manner, six other Schiff-base-type liquid crystal silanes were produced by reacting the γ-isocyanatopropyltrimethoxysilane with 10 parts of different hydroxybenzilidine compounds as summarized in Table I wherein there is also shown the mesophase range for each which were determined also as above. In run number 6 of Table I, γ-isocyanatopropyltriethoxysilane was used instead of the trimethoxysilane.

TABLE I

| Run # | Product | Hydroxybenzilidine compound | Mesophase Range (°C.) | Alkoxy-Silane (pbw) |
|---|---|---|---|---|
| 1 | R—⟨◯⟩—C(H)=N—⟨◯⟩—OCCH$_3$ | HO—⟨◯⟩—CH=N—⟨◯⟩—COCH$_3$ | 72–120 | 8.5 |

TABLE I-continued

| Run # | Product | Hydroxybenzilidine compound | Mesophase Range (°C.) | Alkoxy-Silane (pbw) |
|---|---|---|---|---|
| 2 | R—⟨O⟩—C=N—⟨O⟩—CN | HO⟨O⟩—CH=N—⟨O⟩—CN | 55–65 | 9.2 |
| 3 | R—⟨O⟩—C=N—⟨OOO⟩ (H) | HO⟨O⟩—CH=N—⟨OOO⟩ | 150–190 | 7 |
| 4 | R—⟨O⟩—C=N—⟨fluorene⟩ (H) | HO⟨O⟩—CH=N—⟨fluorene⟩ | 94–120 | 7.1 |
| 5 | R—⟨O⟩—C=N—⟨fluorenone⟩ (H) | HO⟨O⟩—CH=N—⟨fluorenone⟩ | 96–130 | 6.8 |
| 6 | R'—⟨O⟩—C=N—⟨O⟩—N(CH₃)₂ (H) | HO⟨O⟩—CH=N—⟨O⟩—N(CH₃)₂ | 82–150 | 10.2 |

R = (CH₃O)₃SiC₃H₆NHCOO—,
R' = (C₂H₅O)₃Si₃C₆HNHCOO—

EXAMPLE 2

There were charged to a one liter, three-neck, round bottom flask equipped with a magnetic stirrer, thermometer, Dean-Stark trap and water condenser and in which there was a nitrogen atmosphere, 25 parts of 2-chloro-4-hydroxybenzoic acid, 600 parts of toluene, 1 part of concentrated sulfuric acid and 0.6 part boric acid. The reaction mixture was refluxed for 72 hours and then cooled. The reaction mixture was stripped under reduced vacuum and the solid product obtained was subsequently recrystallized from toluene. There was obtained 11.3 parts of magenta colored crystals having a melting point of from 153° C.–154° C. The product, 2-chloro-4-hydroxy-(p-acetylphenyl) benzoate was characterized by infra-red spectroscopy.

There were charged to a 200 ml, one-neck, round bottom flask equipped with a magnetic stirrer, water condenser and in which there was a nitrogen atmosphere, 10 parts of the 2-chloro-4-hydroxy-(p-acetylphenyl) benzoate prepared above, 7.4 parts of γ-isocyanatopropyltrimethoxysilane, 0.5 part of triethylamine and 40 parts of tetrahydrofuran. The reaction mixture was refluxed for 6 hours and then cooled. The solvent was subsequently removed by vacuum stripping and the liquid crystal product, structurally characterized by infra-red spectroscopy and carbon-13-nuclear magnetic resonance spectroscopy, had the structure:

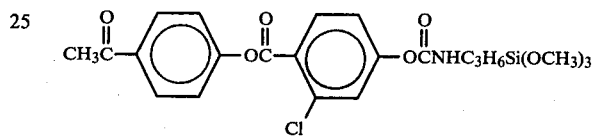

The liquid crystal had a mesophase of from 110° C. to 200° C.; by variable temperature photomicroscopy and differential scanning calorimetric analyses.

In a similar manner, three other ester-type liquid crystal silanes were produced by reacting γ-isocyanatopropyltrimethoxysilane with 10 parts of different 2-chloro-4-hydroxy-(p-acetylphenyl) compounds as summarized in Table II wherein there is also shown the mesophase range for each, which were determined also as above.

TABLE II

| Run # | Product | p-Acetylphenyl Compound | Mesophase Range (°C.) | Alkoxy-silane (pbw) |
|---|---|---|---|---|
| 1 | ⟨O⟩—OOC—⟨O⟩(Cl)—OOCNHC₃H₆Si(OCH₃)₃ | ⟨O⟩—OOC—⟨O⟩(Cl)—OH | <24–55 | 8.3 |
| 2 | Cl—⟨O⟩—OOC—⟨O⟩(Cl)—OOCNHC₃H₆Si(OCH₃)₃ | Cl—⟨O⟩—COO—⟨O⟩(Cl)—OH | <25–155 | 7.2 |
| 3. | CH₃O—⟨O⟩—OOC—⟨O⟩(Cl)—OOCNHC₃H₆Si(OCH₃)₃ | CH₃O—⟨O⟩—OOC—⟨O⟩(Cl)—OH | <25–49 | 8.4 |

EXAMPLE 3

There were charged to a 250 ml, three-neck flask equipped with a mechanical stirrer, thermometer, water condenser with nitrogen by-pass and dropping funnel, 19.3 parts of cholesterol, 2 parts of triethylamine and 80 parts of dioxane. Thereafer there was added 10.3 parts of γ-isocyanatopropyltrimethoxysilane in a dropwise manner. The reaction mixture was refluxed for 24 hours and then cooled to room temperature. The liquid crystal product was identified structurally by infrared spectroscopy and carbon-13-magnetic resonance spectroscopy and had the structure:

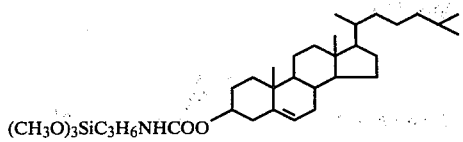

(CH₃O)₃SiC₃H₆NHCOO

The liquid crystal had a mesophase of from 25° C. to 30° C; by variable temperature photomicroscopy and differential scanning calorimetric analyses.

EXAMPLE 4

There were charged to a 200 ml one-neck round bottom flask equipped with a magnetic stirrer and water condenser and having a nitrogen atmosphere, 12 parts of N,N-dimethylamino-4,4′-azodianiline, 10.3 parts of γ-isocyanatopropyltrimethoxysilane, 0.5 part of triethylamine and 40 parts of tetrahydrofuran. The reaction mixture was heated at reflux for 6 hours and then cooled to room temperature. The solvent was then removed by vacuum stripping. The liquid crystal product was identified by infra-red spectroscopy and carbon-13-nuclear magnetic resonance spectroscopy and had the structure:

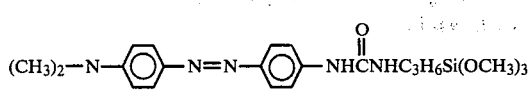

The liquid crystal had a mesophase of from 93° C. to 120° C.; by variable temperature photomicroscopy analysis.

In a similar manner, five other azo-type liquid crystal silanes were produced by reacting γ-isocyanatopropyltrimethoxysilane with 10 parts of different azo compounds as summarized in Table III wherein there is also shown the mesophase range for each, which were determined also as above. In run 190 5, γ-isocyanatopropyldimethylmethoxysilane was used instead of the -trimethoxysilane.

argon atmosphere, 15 parts of p-aminostyrene, 17.3 parts of p-methoxybenzaldehyde and 200 parts of isopropanol. The reaction mixture was stirred at room temperature for 24 hours. Initially the reaction mixture was clear, however, the flask gradually was filled with small flaky crystals upon stirring. The crystals were then recrystallized from absolute ethanol and vacuum dried. There were obtained 26.3 parts of product having a melting point of 83° C.-85° C. The product, p-methoxy-benzilidine-p-vinylaniline, was characterized by infra-red spectroscopy and proton nuclear magnetic resonance spectroscopy.

There were charged to a 250 ml, three-neck round bottom flask equipped with a mechanical stirrer thermometer, dropping funnel and water condenser and having an inert nitrogen atmosphere, 6 parts of the p-methoxy-benzylidine-p-vinylaniline prepared above, 1.98 parts of γ-methacryloxypropyltrimethoxysilane, 110.0 parts of dioxane and 0.1 parts of azobisisobutyronitrile catalyst. The reaction mixture was heated at 92° C. for 16 hours and then cooled to room temperature. The dioxane solvent was then removed by vacuum stripping. The product contained pendant trimethoxysilyl groups was characterized by infra-red spectroscopy and carbon-13-nuclear magnetic resonance spectroscopy. A mesophase was observed at from 65° C. to 92° C. by variable temperature microscopy. The polymeric liquid crystal silane had the chemical structure:

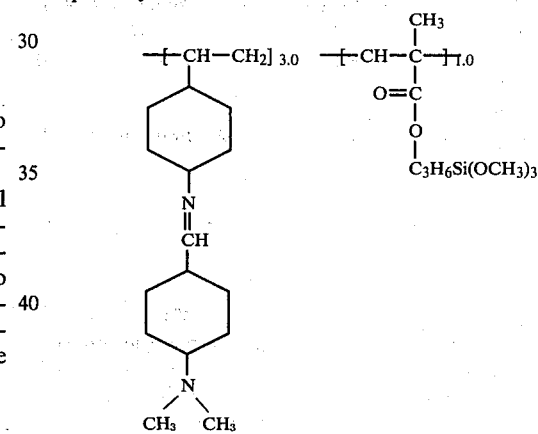

TABLE III

| Run # | Product | Azo compound | Mesophase Range (°C.) | Alkoxy-silane(pbw) |
|---|---|---|---|---|
| 1 | ⟨O⟩-N=N-⟨O⟩-NHCNHC₃H₆Si(OCH₃)₃ (O=) | ⟨O⟩-N=N-⟨O⟩-NH₂ | <25-75 | 10.4 |
| 2 | ⟨O⟩-N=N-⟨O⟩-OOCNHC₃H₆Si(OCH₃)₃ | HO-⟨O⟩-N=N-⟨O⟩ | 50-70 | 10.3 |
| 3 | ⟨O⟩-N=N-⟨O⟩(⟨O⟩)-OOCNHC₃H₆Si(OCH₃)₃ | ⟨O⟩-N=N-⟨O⟩(⟨O⟩)-OH | 128->200 | 8.3 |
| 4 | O₂N-⟨O⟩-N=N-⟨O⟩-OOCNHC₃H₆Si(OCH₃)₃ | HO-⟨O⟩-N=N-⟨O⟩-NO₂ | 55-170 | 7.8 |
| 5 | (CH₃)₂N-⟨O⟩-N=N-⟨O⟩-NHCNHC₃H₆SiOCH₃ (O=, (CH₃)₂) | H₂N-⟨O⟩-N=N-⟨O⟩-N(CH₃)₂ | 88-140 | 6.06 |

EXAMPLE 5

There were charged to a 500 ml, three-neck round bottom flask equipped with a mechanical stirrer, thermometer and water condenser and having an inert It was a slightly yellow solid at room temperature and had a molecular weight of from about 20,000 to about 50,000.

EXAMPLE 6

There were charged to a 100 ml beaker one part of the 4-N,N-dimethylamino-4-N'-γ-trimethyoxysilyl-propylureidoazodianiline prepared in Example 4, 10 parts of tetrahydrofuran and one part of glacial acetic acid. While this mixture was stirred, 38 parts of distilled water was added slowly in one gram increments. After this addition was complete, six microscope slides, each measuring 75 mm×25 mm, were immersed in the mixture, two at a time, for 30 minutes each, removed and dried at 80° C. for 24 hours. The resulting film was visible and was at least several monolayers thick.

The coated slides were soaked in dimethylsulfoxide at 80° C. for 24 hours; the film was not removed. Also, the film could not be removed from the slides by rubbing. This test involves rubbing the slide with a paper towel while the slide lies flat on a bench top. The rubbing is done by hand using moderate pressure. Approximately 30–40 strokes are used. Variable temperature photomicroscopy showed the presence of a mesophase at from 160° C. to 270° C. The change in mesophase range from that reported in Example 4 is due to the hydrolysis of the silane ester group in the film. The mesophase range reported here is that of a liquid crystal silane hydrolyzate. This example establishes that the liquid crystal silane of this invention can be directly chemically bonded to a substrate.

We claim:

1. A liquid crystal compound of the general formula

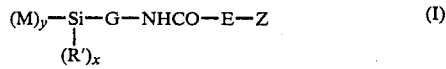

wherein y is an integer having a value of from 1 to 3; x is an integer having a value of from 0 to 2; the sum of x and y is 3 M is methoxy, ethoxy, chloro or dimethylamino; R' is hydrogen, methyl or ethyl; G is alkylene having from 2 to 4 carbon atoms, or arylene or aralkylene having from 6 to 8 carbon atoms; E is —O— or —NH—; and Z is a group of the formula:

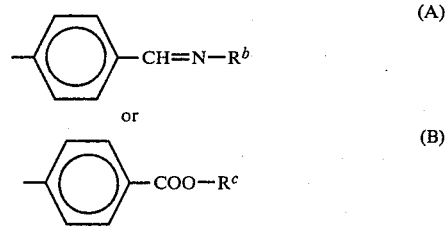

wherein $R^b$ is an unsubstituted or substituted phenyl, fluorenyl, fluorenonyl or anthracenyl group; $R^c$ is an unsubstituted or substituted phenyl group; wherein the substituents on said groups can be chloro, nitro, methylthio, bromo, iodo, tertiary amino, acyl having from 2 to 12 carbon atoms, dialkylamino in which the alkyl group has from 1 to 5 carbon atoms, alkoxy having from 1 to 6 carbon atoms, alkyl having from 1 to 10 carbon atoms, cyano, esters which may contain substituted aryl or aralkyl moieties of from 1 to 12 carbon atoms or carbonates containing an alkyl group of from 1 to 10 carbon atoms.

2. A liquid crystal compound as claimed in claim 1 of the formula:

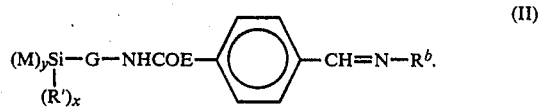

3. A liquid crystal compound as claimed in claim 1 of the formula:

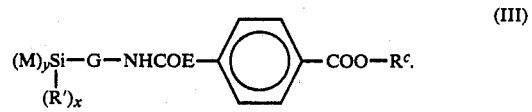

4. A liquid crystal compound as claimed in claim 2 of the formula:

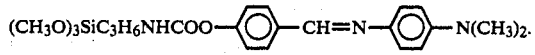

5. A liquid crystal compound as claimed in claim 2 of the formula:

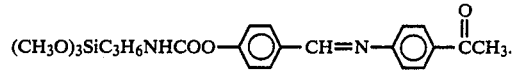

6. A liquid crystal compound as claimed in claim 2 of the formula:

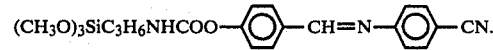

7. A liquid crystal compound as claimed in claim 2 of the formula:

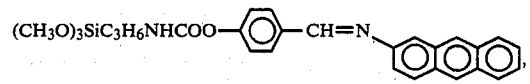

8. A liquid crystal compound as claimed in claim 2 of the formula:

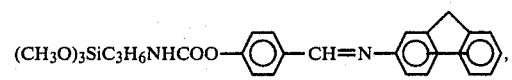

9. A liquid crystal compound as claimed in claim 2 of the formula:

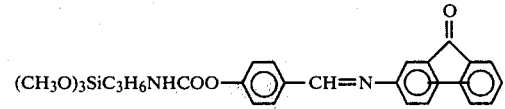

10. A liquid crystal compound as claimed in claim 2 of the formula:

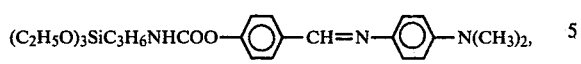
11. A liquid crystal compound as claimed in claim 3 of the formula:
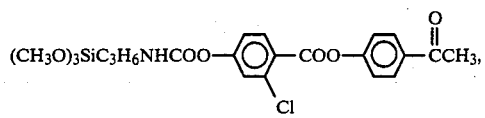
12. A liquid crystal compound as claimed in claim 3 of the formula:
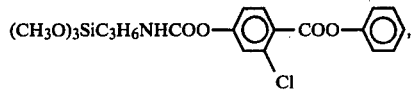
13. A liquid crystal compound as claimed in claim 3 of the formula:
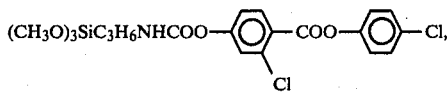
14. A liquid crystal compound as claimed in claim 3 of the formula:
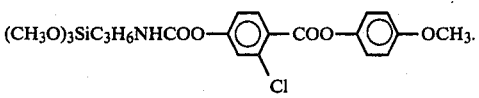
* * * * *